US005672493A

United States Patent [19]
Kopelovich

[11] Patent Number: 5,672,493
[45] Date of Patent: Sep. 30, 1997

[54] DE NOVO INDUCTION OF CELLS EXHIBITING CHARACTERISTICS OF MACROPHAGES UTILIZING FELINE SARCOMA VIRUS

[76] Inventor: Levy Kopelovich, 6630 Burning Tree Dr., Seminole, Fla. 34647

[21] Appl. No.: 135,390

[22] Filed: Oct. 8, 1993

Related U.S. Application Data

[63] Continuation-in-part of Ser. No. 845,298, Mar. 3, 1992, abandoned, which is a continuation-in-part of Ser. No. 488,923, Mar. 5, 1990, abandoned, which is a continuation-in-part of Ser. No. 299,280, Jan. 19, 1989, abandoned.

[51] Int. Cl.$^6$ ............... C12N 5/10; C12N 5/00; A61K 48/00
[52] U.S. Cl. ............ 435/172.3; 424/93.2; 424/93.21; 435/240.1; 435/240.2
[58] Field of Search ............... 435/240.1, 240.2, 435/172.2, 172.3; 424/93.2, 93.21

[56] References Cited

PUBLICATIONS

S. D. Fowler et al. (1985) Ann. New York Acad. Sci. 454:79–90.
K. Frei et al. (1986) The J. of Immunol. 137(11):3521–3527.
R. Andreesen et al. (1983) J. Immunol. Methods 56:295–304.
J. H. Lee et al. (1994) Hematol. Oncol. Clin. North America 8(6):1203–1221.
J. Bartholeyns et al. (1991) Anticancer Research 11:1201–1204.
L. Kopelovich (1992) Eur. Cytokine Network 3(1):63–69.
R. D. Schrier et al. (1990) J. of Virol. 64(7):3280–3288.

*Primary Examiner*—Mindy Fleisher
*Assistant Examiner*—Johnny F. Railey, II
*Attorney, Agent, or Firm*—Caesar, Rivise, Bernstein, Cohen & Pokotilow, Ltd.

[57] ABSTRACT

This invention relates to cells that demonstrate characteristics of tissue macrophages (CCTM), including all substances obtained therefrom, such CCTM are induced from human fibroblasts (HF) by the Snyder-Theilen feline sarcoma virus (ST:FeSV(FeLV)) and are used for the treatment of immunodeficient states. A method for the de novo induction of cells that demonstrate characteristics of tissue macrophages (CCTM) from human fibroblasts (HF), said method comprising isolating and converting HF cultures from human organs, most conveniently skin, performing transformation assays on said HF cultures by transducing with said ST:FeSV(FeLV)-derived DNA sequences, including the corresponding gene products, to demonstrate conversion of HF to CCTM, and to establish the objects and advantages for the production and use of CCTM and CCTM-associated substances in molecular immunotherapy, somatic cell therapy, and gene therapy.

2 Claims, 6 Drawing Sheets

DE NOVO INDUCTION OF CELLS EXHIBITING CHARACTERISTICS OF MACROPHAGES UTILIZING FELINE SARCOMA VIRUS

RELATED APPLICATIONS

This application is a continuation-in-part of application Ser. No. 07/845,298 filed on Mar. 3, 1992 (now abandoned), which is a continuation-in-part application of application Ser. No. 07/488,923 filed on Mar. 5, 1990 (now abandoned), which is a continuation-in-part of application Ser. No. 07/299,280 filed on Jan. 19, 1989 (now abandoned), the entire disclosures of which are incorporated by reference herein.

SPECIFICATION

1. Technical Field

This invention is in the field of molecular immunotherapy and, more particularly, relates to the specific conversion of human fibroblasts (HF) into cells that demonstrate characteristics of tissue macrophages (CCTM) by transduction with the Snyder-Theilen Feline Sarcoma virus (ST:FeSV (FeLV)), wherein the newly formed CCTM, including all substances expressed therefrom, can be used to control immunodeficient states, including infection/inflammatory conditions.

2. Background Art

Development of drug therapies depends on the establishment of drug specificity, high efficacy, and an acceptable therapeutic index. The term "biologic response modifiers" has been applied to treatments using immunologic reagents and other substances derived from biologic sources to distinguish these from conventional surgical treatment, radiation therapy, and chemotherapy. Thus, immunologic approaches for the treatment of cancer, HIV/ARC, and immune compromised patients, including infection/inflammatory conditions, are being actively pursued. For example, the development of cloned recombinant human gene products, including granulocyte-macrophage colony stimulating factor (GM-CSF), three species of interferon (IFN), interleukin-2 (IL-2), and tumor necrosis factor-α (TNF-α) has led to their testing in clinical trials, albeit with varying degrees of success (Lotze, M. T. and Rosenberg, S. A., CA-A.J. Clinicians 38:68–94 (1988), Culliton, B. J., Nature 354:429 (1991)). These clinical trials included the effects of IFN(s) on hematologic malignancies, including CML, hairy cell leukemia, non-Hodgkin's lymphoma, and cutaneous T-cell lymphoma, as well as administration of IL-2, GM-CSF, lymphokines-activated killer cells (LAK), tumor infiltrating lymphocytes (TIL), and TNF-α for therapy of solid tumors. Specific examples of passive immunotherapy include development of monoclonal antibodies, LAK, TIL transduced with the TNF gene, activated macrophages, and the use of autologous and allogeneic bone marrow transplants (Lotze, M. T. and Rosenberg, S. A. CA-A.J. Clinicians 38:68–94 (1988), Culliton, B. J., Nature 354:429 (1991); Scientific Am. 269:1–164 (1993); Fradd, B. R. and Lanstra, R. Gen. Eng. News 13:26 (1993); Heil, M. Gen. Eng. News 13:1 (1993)).

Tissue macrophages (TM) are derived from the mesenchyme (HAM, A. W., Histology, Chapter II, J. B. Lippincott Co. (1986); Heppner, G. H. and Fulton, A. M. (eds.) Macrophages and Cancer, CRC Press, Boca Raton, pp 1–247 (1988); Hardy, J. D., Ann. Surg. 205:445–455 (1988)). TM and TM-derived cytokines play a central role in cell mediated immunity. In addition to their regulatory functions, they are involved in the initiation of immune responses as antigen presenting cells, and in the effector phase as inflammatory, microbicidal and tumoricidal cells (Heppner, G. H. and Fulton, A. M. (eds) Macrophages and Cancer, CRC Press, Boca Raton, pp 1–247 (1988); Cohen, S. (ed) Lymphokines and the Immune Response, CRC Press, Boca Raton, pp 1–279 (1990); Lopez-Berenstein, G. and Klostergaard, J. (eds) Mononuclear phagocytes in cell biology, CRC Press, Boca Raton, pp 1–239 (1993)). Although a few agents have been found to activate TM in situ, the therapeutic efficacy and specificity of these macrophage-activating agents, singly or in combination is, in general, very low. The term "activation" is used herein to mean enhanced function of existing populations of macrophages. Adoptive immunotherapy of solid tumors with activated macrophages has also been attempted, albeit with limited success (Andreesen, R. et. al., Cancer Res. 50:7450–7456 (1990); Bartholeyns, J. et. al., Anticancer Res. 11:1201–1204 (1991)).

GENERAL INTRODUCTION TO THE PRESENT INVENTION

The present invention relates to genes that are believed to be involved in the induction (reprogramming) of human cell differentiation (Kopelovich, L., Mol. Carcinogenesis 8:3–6 (1993)). The term "induction/conversion" is used herein to mean the de novo production of CCTM. The term "proto-oncogene" is used herein to mean a genetic sequence residing in the genome of an unperturbed cell which, if altered in the appropriate manner, has the potential of becoming an oncogene. The term "oncogene" is used herein to mean a genetic sequence whose expression within a cell induces that cell to convert from one cell phenotype to another. For example, ras-derived oncogenes occurring in oncornaviruses caused the specific conversion of cultured HF to adipocytes in the presence of glucocorticosteroids (Kopelovich, L. et al., Exptl. Cell Biol. 54:25–33 (1986); Kopelovich, L. Exptl. Cell Biol. 55:276–280 (1987); Kopelovich et al., Cancer Invest. 5:567–579 (1987)). Thus, activation of proto-oncogenes, in at least certain instances, may represent a physiologic process whereby the cellular homolog of ras, for example, upon activation induces conversion of HF to adipocytes in the presence of endogenous glucocorticosteroids.

The present invention describes the specific conversion of cultured HF into cells that demonstrate characteristics of TM (CCTM) by ST:FeSV(FeLV). Conversion of HF to CCTM was due to a specific effect by the transforming ST:FeSV oncogene, v-fes. Neither a closely related feline sarcoma virus, e.g., Gardner-Arenstein (GA):FeSV, nor unrelated feline sarcoma viruses, e.g., McDonough (SM):FeSV, Gardner-Rasheed (GR):FeSV, Hardy-Zuckerman-4 (HZ4):FeSV, or a variety of other oncornaviruses, including Kirsten murine sarcoma virus (KiMSV), Harvey murine sarcoma virus (HaMSV), Balb murine sarcoma virus (BaMSV), Molony murine sarcoma virus (MoMSV), Abelson murine sarcoma virus (AbMSV), and Simian sarcoma virus (SSV), caused this conversion.

Several well-characterized strains of feline sarcoma virus (FeSV) have been isolated from fibrosarcomas of domestic cats (Snyder, S. P. and Theilen, G. H., Nature 221:1074–1075 (1969); Gardner, M. B., et al., Nature 226:807–809 (1970); McDonough, S. K., et al., Cancer Res. 31:953–956 (1971); Irgens, K., et al., C. R. Acad. Sci. 26:1783–1786 (1973); Besmer, P., et al., Nature 320:415–421 (1986); Rasheed, S., et al., Virology 117:238–244 (1982)). Each of these is a genetic recombinant formed between a feline leukemia virus (FeLV) vector and protooncogene sequences present in normal cat cellular DNA. At least six different viral oncogenes have now been identified among the various FeSV strains. Three of these oncogenes (fes/fps, abl, and sis) were also found in the genomes of viruses isolated from other animals (for review see Weiss, R. et al. (eds) RNA Tumor Viruses, Cold Spring Harbor Press, Vol. 1 (pp 1–1292) 1984) and Vol. 2 (pp 1–1233) (1985).

Nucleic acid hybridization experiments first demonstrated the presence of similar viral oncogene sequences (now designated v-fes) within the ST: and GA:FeSV genomes. V-fes also shows a significant degree of nucleic acid sequence homology to the transforming gene v-fps, of the defective avian sarcoma viruses, FuSV and PRCII. The v-fes sequences are inserted in-frame into the viral gag gene, leading to the formation of polyproteins encoded by the fused gag and v-fes, with antigenic determinants provided by the amino-terminal domain of gag. Other antigenic reactivities are presumably encoded by v-fes. Differences in molecular weights of polyproteins produced by different FeSV strains are accounted for by nucleotide sequence differences, affecting both gag and v-fes, which occur near the 5' sites of recombination between FeLV-derived and c-fes-derived sequences. Coding differences in this region between c-fes and v-fes are unlikely to be critical for transforming activity, since human c-fes can replace at least 80% of v-fes from its 3' end without loss of biological function (for review see Weiss, R. et al. (eds) RNA Tumor Viruses, Cold Spring Harbor Press, Cold Spring Barbor, 2:pp 294–355 (1985)).

Both ST:FeSV p85 and GA:FeSV p110 are associated with a protein kinase activity specific for tyrosine residues (for review, see Weiss, R. et al., (eds) RNA Tumor Viruses, Cold Spring Harbor Press, Cold Spring Harbor, 2:pp 294–355 (1985). In vivo, the polyproteins are themselves phosphorylated on tyrosine at a single preferred site. V-fes appears able to transform mouse cells upon transfection with the plasmid construct, although the size of the resulting product was not examined (Even, J. et al., J. Virol. 45:1004–1016 (1983); Hampe, A. et al., J. Virol 45:466–472 (1983); Hampe, A. et al., Cell 30:775–778 (1982); Weiss, R. et al, (eds) RNA Tumor Viruses, Cold Spring Harbor Press, Cold Spring Harbor, 2:pp 1011–1013 (1985)). Cells transformed by ST: and GA:FeSV also exhibit a marked elevation in the levels of tyrosine phosphorylation of other proteins. Candidate targets for the fes kinase include the 36-kD protein first found in cells transformed by v-src, a 81-kD protein also phosphorylated after EGF treatment, glycolytic enzymes (enolase and phosphoglycerol mutase), and a 150-kD glycoprotein with serine kinase activity.

There have been no experiments prior to this work describing the direct conversion of human cells, specifically HF, to TM by ST:FeSV(FeLV), or by its pseudo types, or by its recombinant forms. Identification of CCTM that were obtained from ST:FeSV(FeLV)-transduced HF cultures was established by (1) light microscopy; (2) scanning and transmission electron microscopy; (3) reattachment; (4) phagocytosis of latex particles and of low density acylated lipoproteins (LDL); (5) expression of non-specific esterases; (6) uptake of lipids; (7) sensitivity to chemotactic substances; (8) expression of TM-associated antigens; (9) expression of TM-associated cytokines; (10) tumoricidal potential (both macrophage-mediated tumor cytotoxicity (MTC), and antigen-dependent cellular cytotoxicity (ADCC)); (11) uptake and replication of leishmania; (12) microbicidal activity. Collectively, these phenotypes describe tissue macrophages as they appear in situ (Lopez-Berenstein, G. and Klostergaard, J. (eds) Mononuclear phagocytes in cell biology, CRC Press, Boca Raton, pp 1–239 (1993)). Furthermore, the EM pattern, the ability to reattach, expression of HLA-DR and of CSF-1R, expression of TNF-$\alpha$ and IFN-$\alpha$, and uptake of leishmania by CCTM are prima facie evidence for identification of tissue macrophages; these are unique to tissue macrophages and are not found in fibroblasts.

This invention describes the specific induction of CCTM from HF, which through transduction with ST:FeSV(FeLV), and in alternative embodiments through recombinant DNA technology, including ST:FeSV(FeLV) sequences and their corresponding gene products, effect this conversion. These viral reagents and their recombinant genes, and gene products are employed to induce CCTM and CCTM-associated substances and they can be used in molecular immunotherapy, including somatic cell therapy and gene therapy.

Somatic cell therapy is defined as the administration to humans of autologous, allogenic, or xenogeneic living cells which have been manipulated or processed ex vivo. Gene therapy is defined as a medical intervention based on modification of the genetic material of living cells. Cells may be modified ex vivo for subsequent administration to humans, or may be altered in vivo by gene therapy given directly to the subject. When the genetic manipulation is performed ex vivo on cells which are then administered to the patient, this is also a form of somatic cell therapy. Initial approaches to gene therapy have involved the alteration and administration of somatic cells. Other techniques can include approaches such as direct administration to patients of retroviral vectors or other forms of genetic material (Scientific Am. 269:1–164 (1993); Fradd, B. R. and Lanstra, R. Gen. Eng. News 13:26 (1993); Heil, M. Gen. Eng. News 13:1 (1993)).

OBJECTS AND ADVANTAGES

Accordingly, several objects and advantages of the present invention are:

(a) to provide a laboratory-based resource that is able produce essentially unlimited number of CCTM, which amount can be modulated as necessary.

(b) to provide a laboratory-based resource that is able to produce essentially unlimited amounts of CCTM-associated immune cytokines.

(c) to provide a laboratory-based resource that is able to express CCTM-associated antigens which are necessary for antigen presentation and for immune cell interaction.

(d) to provide a laboratory-based resource that is able to produce CCTM-derived cell adhesion molecules.

(e) to provide a laboratory-based resource that is able to produce CCTM-derived growth factors which modulate tumor cell growth.

(f) to provide a laboratory-based resource that is able to control infection of macrophages by parasitic organisms.

(g) to provide a laboratory-based resource that is able to produce CCTM-derived antibiotic substances.

(h) to provide a laboratory-based resource of CCTM for use in molecular immunotherapy, somatic cell therapy, and gene therapy.

(i) to provide a laboratory-based resource that permits the use of autologous as well as allogeneic preparations of CCTM.

(j) to provide a laboratory-based resource that is entirely independent of the body's ability to produce TM.

(k) to provide a laboratory-based resource that can supplement and otherwise augment the immune system when appropriate.

Further objects and advantages will demonstrate that the specific induction of CCTM, and subsequent activation of CCTM and of tissue macrophages (TM) by their respective cytokines, including direct interaction of CCTM/TM and of CCTM/TM-derived cytokines with lymphocytes, fibroblasts, endothelial cells, polymorphonuclear leucocytes, and blood producing cells of the bone-marrow would create a powerful and, heretofore not obtainable, immunotherapeutic modalities to fight cancer, HIV/ARC, and immune compromised syndromes, including infection/inflammatory conditions.

Still further objects and advantages will become apparent from a consideration of the ensuing description and figures.

BRIEF DESCRIPTION OF THE FIGURES

The present invention may be more fully understood by reference to the following detailed description of the invention, examples of the invention, and the appended figures in which.

DETAILED DESCRIPTION OF THE INVENTION

Figure 1:
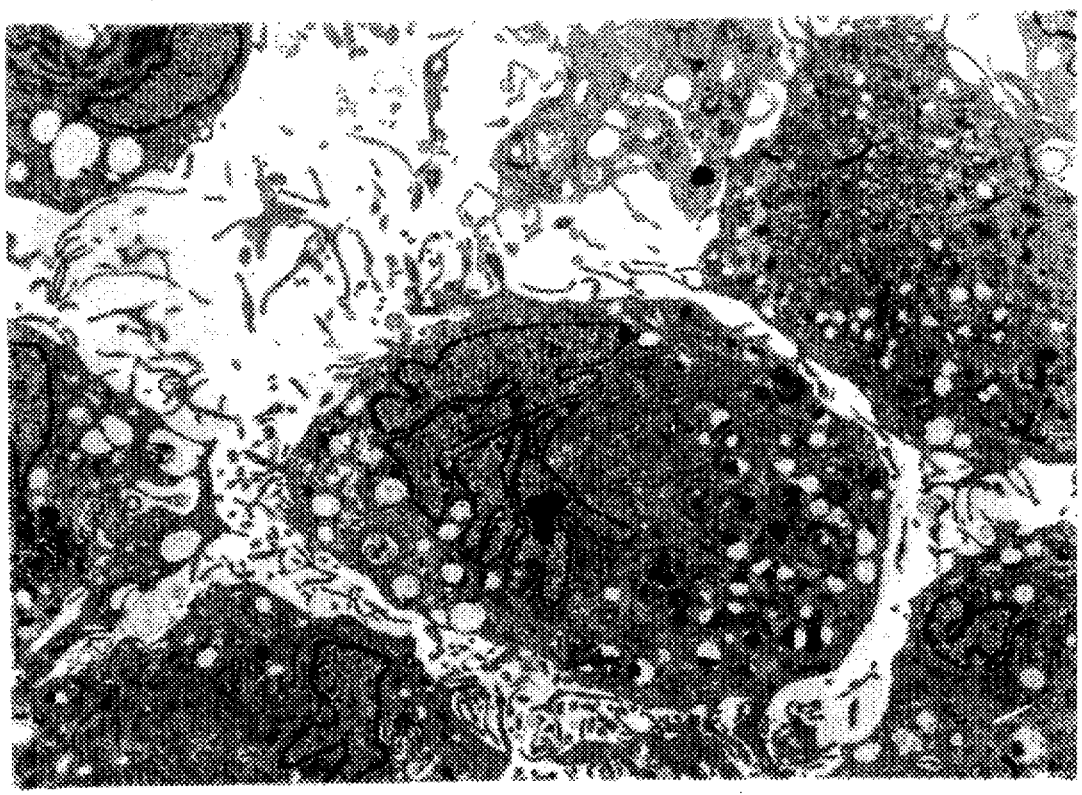
FIGS. 1 and 2 represents the morphology of non-transduced HF and of CCTM by TEM. The CCTM are seen as round cells with short, blunt, cytoplasmic projections, and no tight junctions. The cytoplasm contains numerous vacuoles with partially digested, amorphic foreign material, many mitochondria, and many lysosomal granules. The nuclei are large slightly irregular, and showing a dispersed chromatic pattern. The non-transduced HF, on the other hand, are seen as small ovoid cells with numerous thin, long, cytoplasmic projections that closely interface with neighboring cells. The cytoplasm contains some mitochondria and lysosomal granules and it is rich in rough endoplasmic reticulum. The nuclei are highly convoluted with slightly coarse chromatin.
Figure 2:
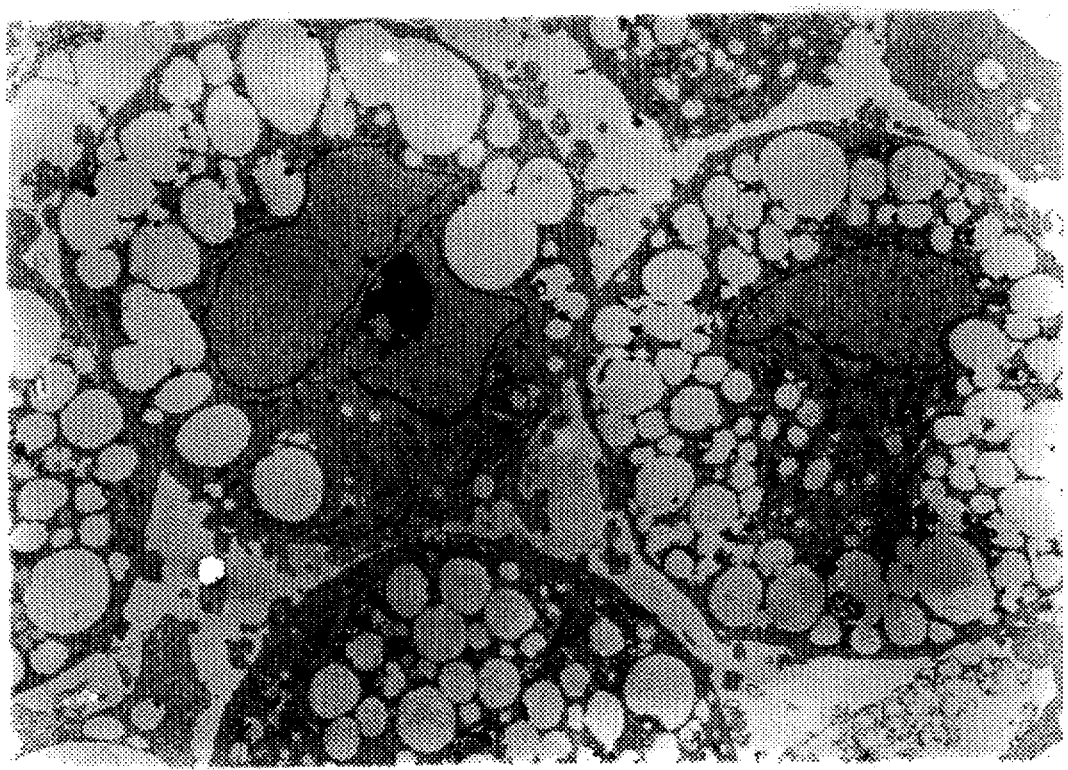
Figure 3:
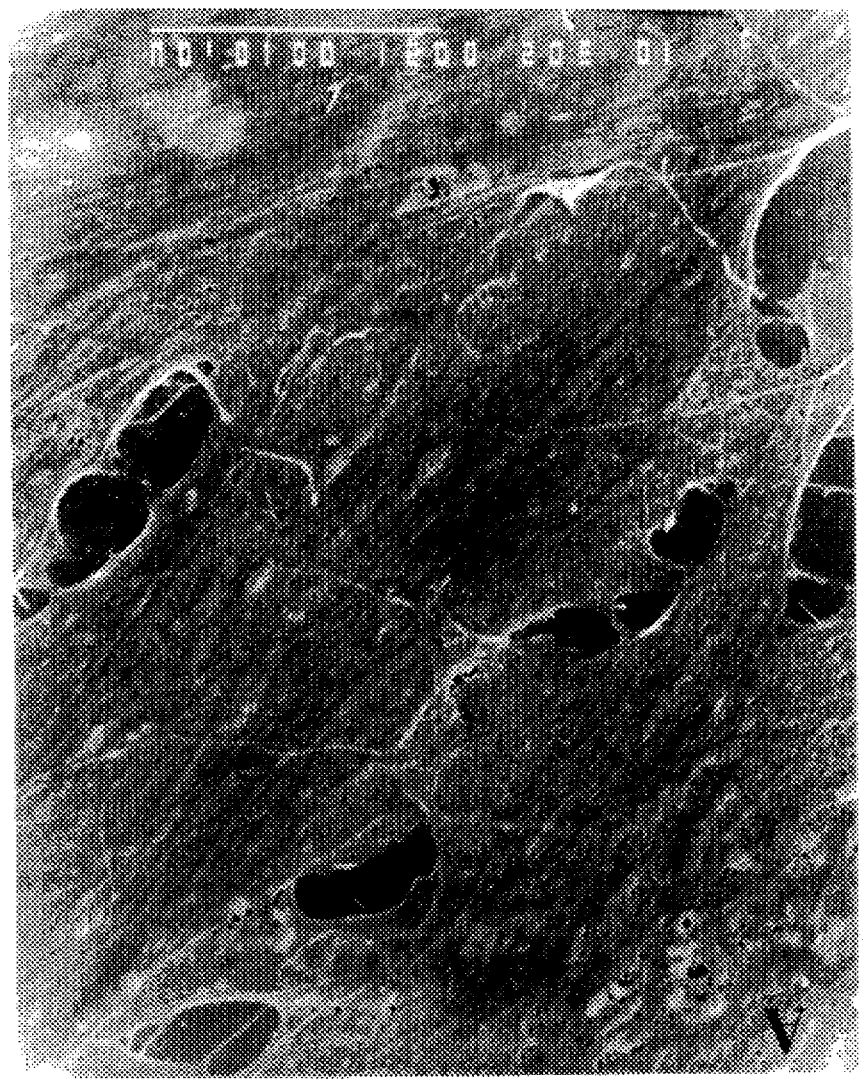
FIGS. 3, 4, 5, and 6 represents the morphology of non-transduced HF and of CCTM by SEM. The CCTM are seen as spherical cells that are covered with an extensive network of microvilli and surface projections, and form no cell-to-cell junctions. The non-transduced HF, on the other hand, exhibit typical fibroblastic morphology. The cells are lacking microvilli, they are growing in close contact with each other, and they appear to be rapidly dividing.
Figure 4:
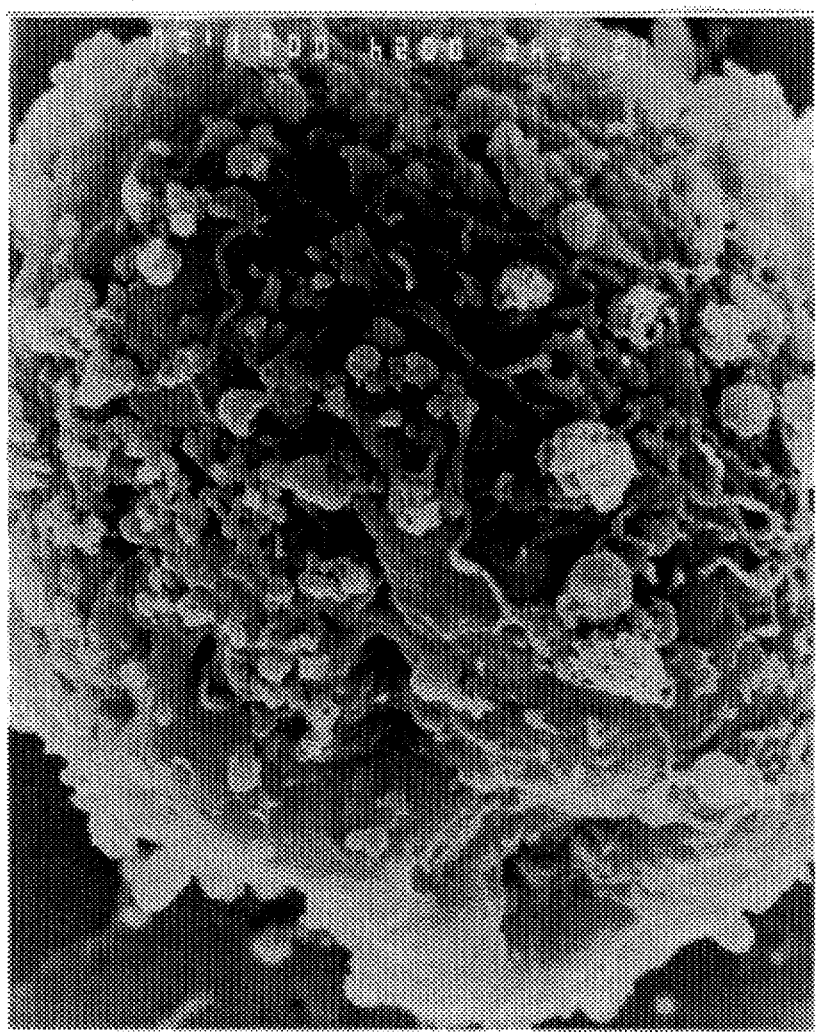
Figure 5:
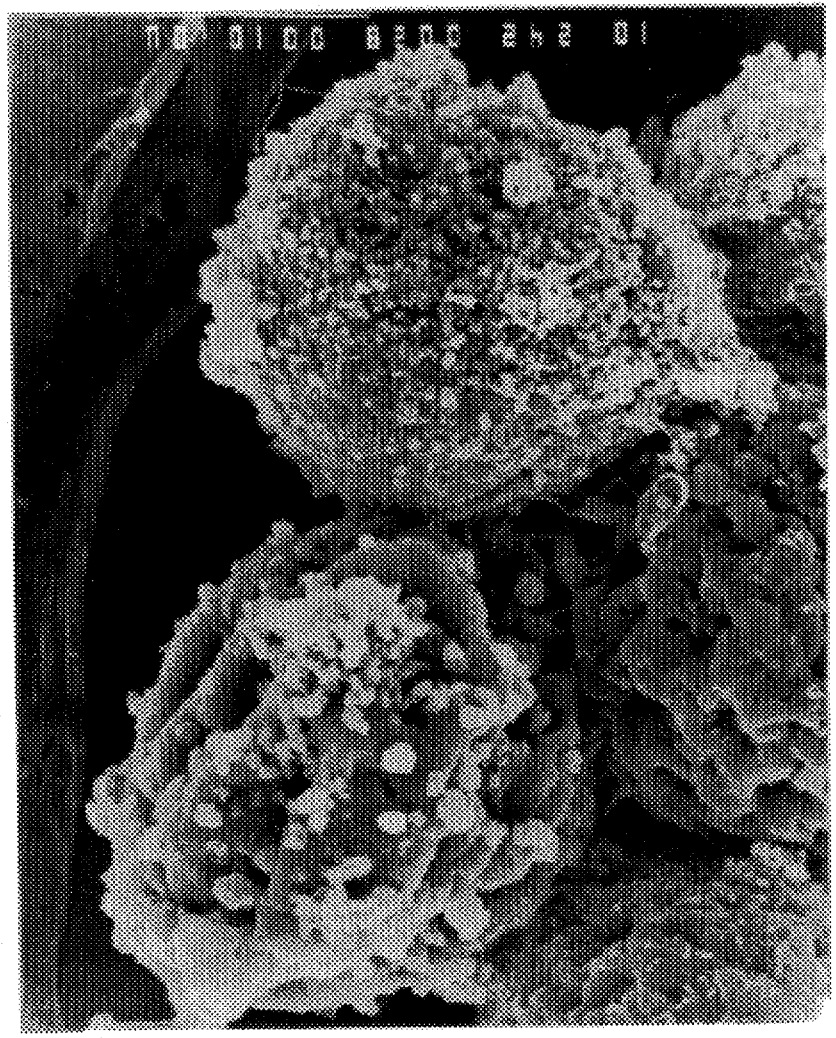
Figure 6:
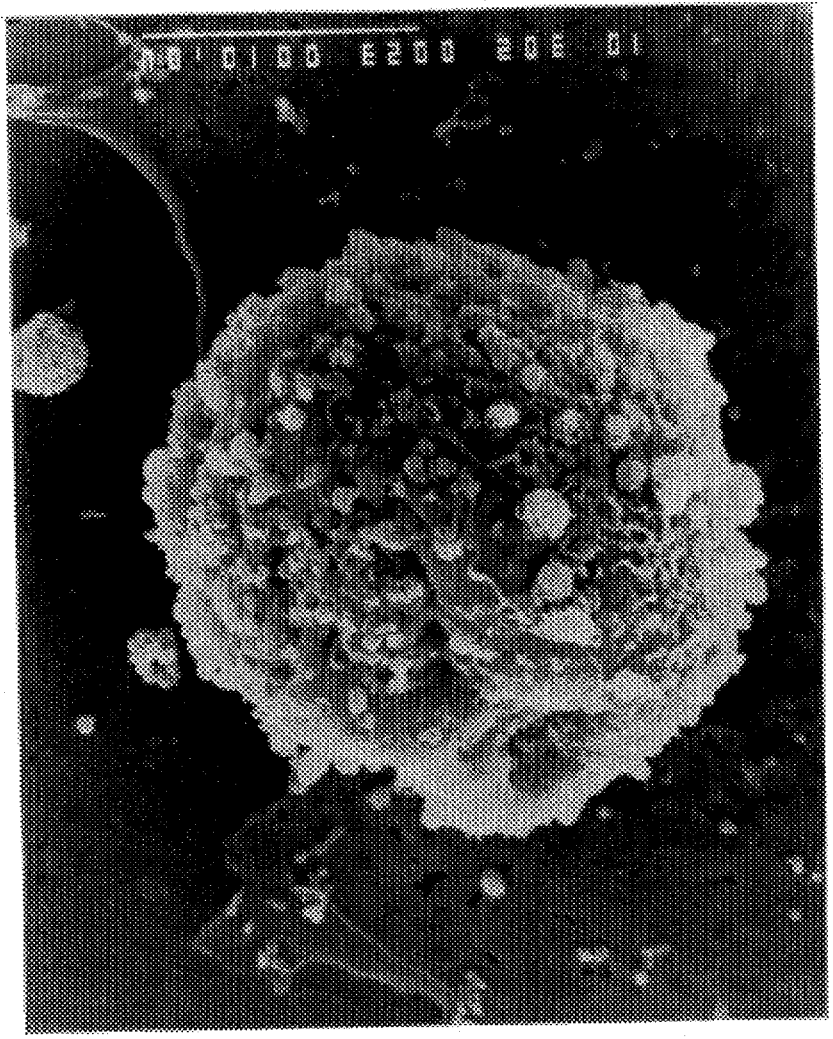

The present invention describes cells that demonstrate characteristics of tissue macrophages (CCTM), including all factors expressed therefrom. HF are obtained from human organs and are transduced with ST:FeSV(FeLV). The newly formed CCTM are small, spherical, migratory cells which are covered with an extensive network of microvilli, and showing no cell-to-cell junctions. The CCTM accumulate lipids, produce non-specific esterases, and they phagocytose latex and LDL particles. The CCTM are stimulated by chemotactic agents and they reattach to solid surfaces by producing extracellular adhesion proteins. The CCTM express macrophage associated antigens, including HLA-DR, and a variety of macrophage-associated immune-cytokines. The CCTM are infected by leishmania and they produce microbicidal substances, and substances that modulate tumor cell growth. This invention, therefore, is based on the close phenotypic/functional association between TM and CCTM, wherein the CCTM can be used as a laboratory based resource for the production of unlimited amounts of TM-associated substances and wherein induction of CCTM can be used in somatic cell therapy and gene therapy.

For the purpose of description, the present invention can be divided into the following stages: (a) preparation of human cell cultures, (b) preparation of virus, (c) virus transduction, (d) determination of the CCTM phenotype, (e) alternative embodiments.

(a) Preparation of cell culture. Tissue biopsies are obtained from clinically uninvolved human organs as well as clinically affected human organs (e.g., inflamed tissues; cancerous tissues). Growing the HF from affected organs is just as routine. Furthermore, the use of HF from clinically affected organs for the induction of CCTM can increase their therapeutic efficacy considerably. This observation is based on the fact that HF taken from an affected site(s) are primed through genetic imprinting that is retained upon conversion to CCTM. This observation is especially appropriate in the case of autologous applications.

In a preferred embodiment of the present invention HF are obtained from minuscule (1 $mm^3$) biopsy specimens of human organs during surgery, or by minor incision involving endoscopic removal of biopsy specimens, including bone marrow. The biopsy specimens are collected in a medium which provides a stable pH for the transport of tissue specimens to the clinical laboratory. Such specimens can be transported from any location, and if necessary, maintained for a period of 7 to 10 days before initiating the cultures. The tissue specimens are placed in a petri dish or a flask and are minced with a surgical scalpel (primary explants). Monolayer cells from such primary explants are maintained in a defined medium such as Earle's balanced salt solution supplemented with 2 mM glutamine, 1% sodium pyruvate, 1% non-essential amino acids (EMEM), and 20% fetal bovine serum (FBS). A portion of these cells is frozen for later use and the remaining cells are used within the first 5–10 passages in culture as described below.

(b) Virus Preparation. In a preferred embodiment, ST:FeSV(FeLV) is used to convert HF to CCTM. ST:FeSV (FeLV) stocks are propagated and plaque purified in a mink (CCL-64) cell line. Tissue culture fluid from near-confluent ST:FeSV-transduced mink (CCL-64) cells is harvested, clarified by low speed centrifugation, and stored in liquid nitrogen. In addition, an infected mink (CCL-64) cell line, that is continuously producing a replication/transformation-competent ST:FeSV(FeLV) is used as a virus source. Virus stocks are assayed for focus formation on mink (CCL-64) indicator cells, and the titer is expressed as focus-forming units per ml. To reduce variability between laboratories, large stocks of "reagent grade" virus, each sufficient for use on HF cultures from at least $1\times10^6$ biopsy specimens can be readily prepared.

(c) Virus Transduction. Virus transduction is performed on HF cultures that are incubated with diethylamineaminoethyl (DEAE) dextran ($2\times10^6$ MW; Pharmacia) for one hour and then infected with appropriately diluted, freshly-thawed, millipore filtered ST:FeSV(FeLV) stock virus with constant shaking for one hour. The virally transduced HF are maintained in EMEM culture medium containing 10% FBS for up to six weeks. CCTM-containing foci generally appear in infected cultures after the first week, and floating CCTM are harvested during the next five weeks at weekly intervals. The harvested CCTM are replated in a EMEM medium containing 10% FBS, and their phenotype is determined. Since, serum constitutes a complex mixture of hormones, growth factors, transport proteins and nutrients, the actual amounts of which may differ from one serum lot to another, the replated CCTM are also incubated in serum-free media (Gibco; M-SFM). The use of M-SFM is particularly advantageous for the determination of extracellular adhesion substances, immune cytokines, substances that modulate tumor cell growth, and antibiotic substances.

(d) Determination of the CCTM phenotype. Transmission electron microscopy (TEM) is carried out on replated CCTM pellets that are fixed in 2.5% buffered glutarylaldehyde, post-fixed in osmiumtetraoxide for one hour, dehydrated in ethanol, and embedded in epoxy. Ultrathin sections are made and contrasted with uranyl acetate/lead acetate, and viewed by TEM.

Scanning electron microscopy (SEM) is done on replated-CCTM pellets that are fixed in 2.5% buffered glutarylaldehyde, dehydrated in ethanol, followed by hexamethyldisilazone, and vacuum dried. The fixed pellets are mounted on specimen stubs that are sputter-coated with gold-palladium, and viewed by SEM.

Phagocytosis is carried out on replated CCTM that are incubated with latex beads (1.1 microns in diameter; Sigma) at a final concentration of 0.005%–0.001% (w/v), or with acylated LDL fluorescent particles (bioprobes) at a final concentration of 10 micrograms per ml for 1–5 hours.

Stimulation of replated CCTM by chemotactic agents is done through addition of chemoattractants at time intervals, following which the culture media is harvested and tested for CCTM-associated cytokines. Alternatively, CCTM are plated on a 12μ filter wherein the lower chamber contains the chemoattractants, and wherein migration of the CCTM across the filter is used to measure their response to said substances.

Esterases and lipids staining are carried out on replated CCTM cultures following removal of the culture media, and a wash with phosphate buffered saline (PBS). The staining protocols include naphthol AS-D chloracetate for specific esterases (Sigma-Kit #91-C, Leder's stain), naphthyl acetate for non-specific esterases (Sigma-Kit #92-A), and 0.2% oil-red-o for lipids staining.

Qualitative determination of CCTM-associated antigens, CCTM-associated cytokines, and CCTM-associated extracellular adhesion molecules is done on CCTM that are plated on glass slides and are fixed with 10% buffered formaldehyde followed by 10% methanol, or paraffin sections of 2.5% glutarylaldehyde-fixed CCTM pellets using the specific antibodies by direct (single-labeled antibody)/indirect (second antibody tagged) immunoperoxidase or immunofluorescence staining. Quantitative determination of macrophage-associated antigens, and macrophage-associated cytokines in the conditioned media and in cell lysates of CCTM is carried out by the "sandwich" enzyme immunoassay technique (ELISA) using commercial kits that are specific for the antigens/cytokines. Determination of CCTM-associated extracellular adhesion molecules is carried out in M-SFM as above.

Oncocytolytic activity, both macrophage-mediated tumor cytotoxicity (MTC) and antibody-dependent cellular cytotoxicity (ADCC), is determined by the release of $^3$H-thymidine from tumor cells that are co-cultured with replated CCTM in 96-well dishes. Mock-infected fibroblasts co-cultured with the tumor cells are used as controls. The CCTM, or mock-infected HF are incubated alone for 3 days in the absence and presence of cytokines. Subconfluent cultures of target cells are pulsed with 25 μCi $^3$H-thymidine (20.0 Ci/mmol, Du Pont) for 24 h, harvested with 5 mM EDTA, washed twice and added to the macrophage or fibroblast cultures to obtain the desired effector to tumor cell ratio in the absence or presence of cytokines. When indicated, an antibody (NRCO-4) directed against the tumor cells is added (ADCC). After 96 h, 10 μl of 1 mg/ml DNAase (Pharmacia) is added to each well, and incubated for 30 additional min at 37° C. A total of 50 μl of supernatant from each well, in duplicates, are then placed in 10 ml of scintillation fluid (Ultima Gold, Packard) and counted in a Packard Tricarb 4640 scintillation counter. Identification of proteins that modulate tumor cell growth is carried out through selective dialysis (range 500–50,000 MW) of CCTM-derived M-SFM, followed by lyophilization, gel permeation on HPLC, resolution and purification of the individual HPLC fractions, and sequencing on an Applied Biosystems 473A protein sequencer.

Infection of CCTM by leishmania major is carried out on replated CCTM that are exposed to one amastigote per single cell in polypropylene tubes at 37° C., 5% $CO_2$, with periodic shaking. Samples of cell suspensions are removed at various times and the percent CCTM with intracellular amastigotes is estimated by microscopic examination of Wright-stained cytosmears. Treatment with antigen-induced cytokines is carried out to determine resistance to infection after about two hours and to determine intracellular killing after about 72 hours. Controls consist of peripheral blood monocyte cultures (PBMC) of HIV-1 and hepatitis B-seronegative donors that are recovered after leukapheresis. This is followed by Ficoll-Hypaque density gradient centrifugation, and separation into monocytes and PBL fractions by countercurrent centrifugal elutriation. Monocyte suspensions are 90–95% pure by cell morphology criteria on Wright-stained cytosmears, by granular peroxidase, and by non-specific esterases. The monocytes are cultured as adherent monolayers ($1\times10^6$ cells/6.4 mm culture well) in 0.2 ml DMEM (Sigma) with 10% heat inactivated $AB^+$ human serum (Sigma), 50 μg/ml gentamicin, 2 mM glutamine, and 1000 U/ml of highly purified human r M-CSF (Cetus). It should be emphasized that monocytes, unlike CCTM, must be activated by M-CSF in order to become infected by L. major. Furthermore, infection by L. major is unique to macrophages and has never been seen in HF.

CCTM-derived antibiotic substances are obtained from serum-free conditioned media that is subjected to selective dialysis, lyophilization, and gel permeation on HPLC. This CCTM-derived serum-free conditioned media is tested against standard bacterial strains (ATCC) as follows:

(1) the bacterial strains are diluted to a 0.5 McFarland units in trypsin soy broth (TSB), and inoculated onto chocolate agar plates (65 mm). Filter paper disks (5 mm) are soaked with the CCTM-derived serum-free conditioned media and are placed in the center of the agar plates. The inoculated plates are incubated for twenty-four hours at 35° C. following which clear inhibited zones around the paper disks are measured.

(2) CCTM-derived serum-free conditioned media is diluted with either TSB or serum-free control media (without CCTM) range 1:1 to 1:1000 in 12×75 mm tubes which are inoculated with stock bacterial cultures (0.5 McFarland units) for twenty-four hours at 35° C. Titers are read to last clear (no growth) tube.

(e) Alternative embodiments. In alternative embodiments of the present invention, the HF are transduced with recombinant DNA sequences from ST:FeSV(FeLV), or are treated with the corresponding recombinant gene products of said DNA sequences that themselves facilitate the conversion of HF to CCTM.

Conveniently, cloning of ST:FeSV(FeLV), and all partial sequences therefrom, are obtained through the use of integrated provirus, unintegrated circular provirus, extracellular infectious virus from ST:FeSV(FeLV)-induced CCTM (a progeny of one cycle of infection of CCTM that represents a purification step), including wild-type virus from continuously producing CCL-64 mink cells, and utilizing both genomic and c-DNA libraries for gene cloning, and for expression of recombinant proteins that are the corresponding gene products of said sequences. The virus is purified and reverse-transcribed, following which the entire viral sequence, and selected sequences therefrom, are cloned for expression in recipient cells, using plasmid constructs by a combination of PCR and restriction fragments subcloning. Since v-fes presumably represents a fusion product with gag polypeptides, inclusion of FeSV with an amphotropic helper is also carried out.

Cloning, expression, protein purification, and characterization, including sequencing are carried out. DNA from CCL-64 mink producer cells and CCTM is digested with restriction endonucleases and is used for custom genetic library in bacteriophage lambda, Lambda-ZAPII. Library construction is according to stratagene standard protocols. Automated dideoxynucleotide chain termination sequences is performed on a Genesis 2000 sequencer. Direct sequencing is performed in both directions after pBluescript plasmid rescue or subcloning into pBluescript. One of the methods for the production of recombinant fusion protein is by the maltose-binding protein, beta galactosidases, protein-A and the FLAG system available from IBL. This is followed by the generation of monoclonal antibodies against the recombinant ST:gag-fes protein, and the monoclonal antibodies are then screened by the SPIT assay. Conveniently, identification of proteins that represent the corresponding gene products of ST:FeSV(FeLV) sequences is also facilitated through the purification from the conditioned medium of cultured HF that have been converted to CCTM by infection with ST:FeSV(FeLV), but which over time have become non-producers for said virus, and through sequence determinations obtained from our own clones, which expression causes conversion of HF to CCTM as set forth in the attached claims.

All cloned sequences are assayed for biological activity. Conveniently, all such sequences are placed in appropriate expression vectors containing regulatory DNA sequences that identify uptake and control expression of same, and are assayed in vitro by transfection, or by electroporation, or by the method of helper-free recombinant retrovirus—mediated transduction for (a) transforming ability (mink cells, HF), (b) ability to convert HF to CCTM, (c) expression of the ST:gag-fes tyrosine kinase protein ($p85_{gag-fes}$) (mink cells, CCTM), and (d) CCTM phenotypes that collectively define TM in situ as follows: (1) light microscopy, (2) scanning and transmission electron microscopy, (3) reattachment, (4) phagocytosis of latex particles and of low density acylated lipoproteins (LDL), (5) expression of non-specific esterases, (6) uptake of lipids (7) sensitivity to chemotactic substances, (8) expression of TM-associated antigens, (9) expression of TM-associated cytokines, (10) tumoricidal potential (both macrophage-mediated tumor cytotoxicity (MTC), and antigen-dependent cellular cytotoxicity (ADCC)), (11) uptake and replication of leishmania, (12) microbicidal activity.

All cloned sequences that, through recombinant retroviruses-mediated transduction, or through transfection, or through electroporation, are able to convert HF to CCTM can be used for gene transfers and for isolation in recipient cells of the corresponding gene products that themselves are able to affect HF conversion to CCTM.

EXAMPLES

Cells that Exhibit Characteristics of Tissue Macrophages (CCTM)

The following examples serve to illustrate the nature of the invention without being a limitation of the scope thereof.

Example 1

Conversion of HF to CCTM is specific to ST:FeSVfFeLV).

HF were obtained from minuscule (1 $mm^3$) biopsy specimens of human skin. The biopsy skin specimens were collected in a medium which provides a stable pH for transport of the tissue specimens to the clinical laboratory. The tissue specimens were placed in a petri dish or a flask and were minced with a surgical scalpel (primary explants). Monolayer cells that grew out from such primary explants were maintained in Earle's balanced salt solution supplemented with 2 mM glutamine, 1% sodium pyruvate, 1% non-essential amino acids (EMEM), and 20% FBS. A portion of these cells was frozen for later use and the remaining cells were used within the first 5–10 passages in culture as described below.

ST:FeSV(FeLV) stocks were propagated and plaque purified in a normal mink (CCL-64) cell line. Tissue culture fluid from near-confluent ST:FeSV-transduced mink (CCL-64) cells was harvested, clarified by low-speed centrifugation, and stored in liquid nitrogen. In addition, an infected mink (CCL-64) cell line, that is continuously producing a replication/transformation-competent ST:FeSV(FeLV) was used as a virus source.

Virus transduction of the cultured HF was performed on HF cultures that were incubated with diethylamineaminoethyl (DEAE) dextran ($2 \times 10^6$ MW; Pharmacia) for one hour and then transduced with appropriately diluted, freshly-thawed, millipore filtered ST:FeSV(FeLV) stock virus with constant shaking for one hour. The virally transduced cells were maintained in EMEM culture medium containing 10% FBS for up to six weeks. CCTM-containing foci generally appeared in infected cultures after the first week and they were scored seven days later.

The extent and specificity of HF conversion to CCTM-containing foci is shown in Table 1. Of all the viruses tested only ST:FeSV(FeLV) produced CCTM.

TABLE 1

Testing of a Variety of Oncornaviruses For the Ability to Induce HF Conversion to CCTM

| Replication Competent Viruses | Total Transformed Foci mean (range) | Macrophage Containing Foci mean (range) | Percent Foci Containing Macrophages |
| --- | --- | --- | --- |
| KiMSV (KiMLV) | 59.2(11–150) | 0 | 0 |
| KiMSV (AP292) | >100 | 0 | 0 |
| HaMSV (AP292) | 39.2 (20–40) | 0 | 0 |
| BaMSV (AP292) | 96.7(74–103) | 0 | 0 |
| MoMSV (MoMLV) | 3.0 (1–6) | 0 | 0 |
| MoMSV (AP292) | >100 | 0 | 0 |
| AbMSV (AP292) | 0 | 0 | 0 |
| ST:FeSV (FeLV) | 65.5(12–200) | 63.2 (10–200) | 96.5 |
| ST:FeSV (AP292) | 0 | 0 | 0 |
| GA:FeSV (FeLV) | 70.5(23–115) | 0 | 0 |
| GR:FeSV (AP129) | 0 | 0 | 0 |
| SM:FeSV (AP129) | 36.0 (10–56) | 0 | 0 |
| SSV (SSAV) | 83.5 (80–85) | 0 | 0 |
| AP129 | 0 | 0 | 0 |
| KiMLV | 0 | 0 | 0 |

TABLE 1-continued

Testing of a Variety of Oncomaviruses For the Ability to Induce HF Conversion to CCTM

| Replication Competent Viruses | Total Transformed Foci mean (range) | Macrophage Containing Foci mean (range) | Percent Foci Containing Macrophages |
|---|---|---|---|
| FeLV | 0 | 0 | 0 |
| SSAV | 0 | 0 | 0 |

Example 2

Conversion of HF from different organs to CCTM by ST:FeSV(FeLV). Biopsies from human organs were obtained during organ specific surgical procedures. The biopsies were about 1 mM$^3$ in size and they were processed in a manner similar to the skin biopsies as outlined in example 1. HF cultures, virus preparation, and virus transduction were carried out as in example 1 wherein the number of CCTM containing foci was determined.

The conversion potential of fibroblasts from the different organs is shown in Table 2. HF from all organs tested converted to CCTM following transduction with ST:FeSV (FeLV), albeit at different efficacies.

TABLE 2

Differences In Conversion Potential of HF To CCTM From Different Organs/Tissues

| Organ/Tissue | Total Transformed Foci | CCTM Containing Foci | Percent Foci With CCTM |
|---|---|---|---|
| Umbilicus | 57 | 56 | 98 |
| Embryo | ND | ND | — |
| Foreskin | >200 | >200 | 100 |
| Prostate | 11 | 7 | 64 |
| Bladder | >175 | >175 | 100 |
| Jejunum | 23 | 18 | 78 |
| Colon | ND | ND | — |
| Spleen | ND | ND | — |
| Lung | 3 | 3 | 100 |

ND = not done.

Example 3

Transmission and scanning electron microscopy of the replated CCTM. Skin biopsies, HF cultures, virus preparation, and virus transduction were carried out as shown in example one. The CCTM were collected from the culture media and they were replated as a homogeneous population of cells. FIG. 1A shows a TEM of non-transduced HF and of replated CCTM, wherein CCTM are seen as round cells that are lacking tight junctions with short, blunt, cytoplasmic projections. The cytoplasm contains numerous vacuoles with partially digested amorphic foreign material, many mitochondria, and many lysosomal granules. The nuclei are large, slightly irregular, showing dispersed chromatic pattern. The non-transduced HF are seen as small, ovoid cells with numerous, thin, long, cytoplasmic projections that closely interface with neighboring cells. The cytoplasm contains some mitochondria and lysosomal granules, and it is rich in rough endoplasmic reticulum. The nuclei are highly convoluted with slightly coarse chromatin. FIG. 1B shows SEM of the non-transduced HF and of the replated CCTM, wherein CCTM are seen as spherical cells that are covered with extensive network of microvilli, and surface projections, forming no cell-to-cell junctions. The non-transduced HF exhibited typical fibroblastic morphology. The cells were lacking microvilli, growing in close contact with each other, and they appear to be rapidly dividing.

Example 4

Expression of macrophage associated antigens on CCTM. Skin biopsies, HF cultures, virus preparation, and virus transduction are as in example 1. Determination of surface antigens was carried out on replated CCTM that were prepared as 10% formaldehyde fixed paraffin blocks, or following fixation in buffered 10% formaldehyde-10% methanol using indirect or direct immunoperoxidase/ fluorescence staining according to manufacturer's recommendations and as described (Azar, H. A. (ed.) Pathology of Human Neoplasms, Raven Press, New York, pp. 1–638, 1988; Harlow, E. D. Lane (eds.) Antibodies, Cold Spring Harbor, Cold Spring Harbor, pp. 1–726, 1988). The data is outlined in Table 3. All tissue macrophage markers, notable among which CSF-1R, stained positive on the surface of CCTM. CSF-1R is generally used as prima facia evidence for the identification of the macrophage phenotype. Factor VIII, an endothelial marker, did not stain CCTM.

TABLE 3

Surface Antigen Phenotype of ST:FeSV(FeLV)-Induced CCTM

| | Culture Conditions | | |
|---|---|---|---|
| Antigen (Antibody) | Antigen Positive Cells | Mock-Infected Fibroblasts | ST:FeSV(FeLV) induced CCTM |
| CD11b (MAC-1) | G, M, NK** | —*** | + |
| CD11c (Leu-M5) | G, M, NK | — | + |
| CD14 (Leu-M3) | M | — | + |
| CD16 (Leu-11b) | NK, G, Mac | — | + |
| HLA-DR* | M, Mac, B | — | + |
| M/M | Mac, Mel | — | + |
| CSF-1 | M, Mac | — | + |
| Factor 8 | Endo | — | — |

*Also determined by FACS
**G = granulocytes, M = monocytes, NK = natural killer cells, Mac = macrophages, B = B-cells, Mel = melanocytes, Endo = endothelial cells.
***(—) denotes not staining; (+) denotes positive reaction; it does not indicate intensity.

Example 5

Expression of macrophage associated cytokines in CCTM. Skin biopsies, HF cultures, virus preparations, and virus transduction are as in example 1. Determination of the cytokines was carried out on replated CCTM that were prepared as 10% formaldehyde fixed paraffin blocks, or as fixation in 10% buffered formaldehyde-10% methanol, or ELISA according to (Azar, H. A. (ed.) Pathology of Human Neoplasms, Raven Press, New York, pp. 1–638, 1988; Harlow, E. D. Lane (eds.) Antibodies, Cold Spring Harbor, Cold Spring Harbor, pp. 1–726, 1988).

The data is outlined in Table 4. With the exception of IL-6, non-transduced HF demonstrated either no cytokine production, or levels of production at least one log less than replated CCTM.

TABLE 4

ELISA Determination of Macrophase-associated Cytokines in ST:FeSV(FeLV)-induced CCTM

| Cytokine | Amount of present in Conditioned medium (pg/10$^5$ cells) |
|---|---|
| IL-1α | 160 |
| IL-1β | 9,840 |
| IL-6 | 6,540 | coincubation period at an effector-to-target cell ration of 5:1. The presence of M-CSF in particular during the coincubation period yielded optimal lysis of the tumor cells. Addition of tumor specific antibody (NRCO-4) substantially increased the cytolytic potential of CCTM. Significantly, coincubation of CCTM with tumor cells in an agar medium, where no direct contact between cells occurs, resulted in inhibition of tumor cell prohibition.

TABLE 4-continued

ELISA Determination of Macrophase-associated Cytokines in ST:FeSV(FeLV)-induced CCTM

| Cytokine | Amount of present in Conditioned medium (pg/$10^5$ cells) |
|---|---|
| TNF-$\alpha$ | 760 |
| GM-CSF | 180 |
| M-CSF | 800 |
| IL-8 | $\leq$10,000 |
| MCP-1 | $\leq$25,000 |
| IFN-$\alpha$* | + |
| TFG-$\beta$* | + |
| PDGF* | + |
| IL-12* | + |

*Determined by immunofluorescence only.

Example 6

Modulation of tumor cell growth by the CCTM. The cytolytic activity, both macrophage-mediated tumor cytotoxicity (MTC) and antibody-dependent cytotoxicity (ADCC), was determined by the release of $^3$H-thymidine from tumor cells that were coincubated with CCTM. Tumor cells alone and non-transduced HF cocultured with the tumor cells were used as controls. The concentration of cytokines during the various incubation conditions were as follows. IFN-gamma (50 U/ml), M-CSF (20 ng/ml), LPS (0.5 μg/ml). Results were expressed as average CPM of $^3$H-thymidine released into the medium.

The results of the effects of CCTM on the colon adenocarcinoma are outlined in Table 5. The results show that CCTM produced significant lysis of the tumor cells after a three day preincubation period followed by a four day

TABLE 5

EFFECT OF ST:FeSV-INDUCED CCTM ON THE LYSIS OF L-180 HUMAN COLON ADENOCARCINOMA CELLS IN THE PRESENCE OF THE MACROPHAGE-SPECIFIC CHEMICAL ATTRACTANT F-MLP

| INCUBATION CONDITIONS | | CPM IN MEDIUM | | | | | | | |
|---|---|---|---|---|---|---|---|---|---|
| | | (A) TUMOR CELLS | | (B) TUMOR CELLS/ FIBROBLASTS | | (C) TUMOR CELLS/ ST:FeSV- INDUCED TM | | C/B % | C/B % |
| PREINCUBTION | COINCUBATION | EXPT 1 | EXPT 2 | EXPT 1 | EXPT 2 | EXPT 1 | EXPT 2 | EXPT 1 | EXPT 2 |
| 0 | 0 | 2064 | 3372 | 1908 | 3376 | 4980 | 8676 | 261 | 257 |
| 0 | LPS | 2072 | 3440 | 1756 | 3224 | 4260 | 9796 | 242 | 303 |
| 0 | IFN-$\gamma$ | 3848 | 4180 | 2564 | 4680 | 4604 | 10340 | 179 | 221 |
| 0 | M-CSF | 1964 | 3600 | 1628 | 3232 | 5244 | 7416 | 322 | 229 |
| 0 | IFN-$\gamma$/M-CSF | 1960 | 4316 | 2080 | 5204 | 5144 | 11008 | 247 | 212 |
| 0 | F-MLP | 2000 | 3456 | 1544 | 2936 | 4356 | 7480 | 282 | 254 |
| 0 | F-MLP + LPS | 1804 | 3184 | 1620 | 2956 | 4832 | 7512 | 298 | 254 |
| 0 | F-MLP + IFN-$\gamma$ | 1964 | 3600 | 1824 | 4696 | 4320 | 9340 | 237 | 199 |
| 0 | F-MLP + M-CSF | 1652 | 2708 | 1628 | 2796 | 4496 | 7036 | 276 | 252 |
| 0 | F-MLP + IFN-$\gamma$/M-CSF | 3008 | 4148 | 1728 | 4528 | 4176 | 10048 | 242 | 221 |
| F-MLP | 0 | — | — | 1664 | 3048 | 2752 | 9032 | 165 | 296 |
| F-MLP | LPS | — | — | 1548 | 2828 | 3124 | 9056 | 201 | 320 |
| F-MLP | IFN-$\gamma$ | — | — | 2056 | 4920 | 3648 | 10080 | 177 | 205 |
| F-MLP | M-CSF | — | — | 1388 | 2712 | 3780 | 8548 | 272 | 315 |
| F-MLP | IFN-$\gamma$/M-CSF | — | — | 1980 | 5292 | 4132 | 9884 | 208 | 187 |
| F-MLP | F-MLP | — | — | 1860 | 3304 | 6664 | 7744 | 358 | 234 |
| F-MLP | F-MLP + LPS | — | — | 1708 | 3088 | 3560 | 8292 | 208 | 268 |
| F-MLP | F-MLP + IFN-$\gamma$ | — | — | 2208 | 4716 | 2872 | 8492 | 130 | 180 |
| F-MLP | F-MLP + M-CSF | — | — | 1480 | 2940 | 2040 | 7324 | 137 | 249 |
| F-MLP | F-MLP + IFN-$\gamma$/M-CSF | — | — | 2404 | 5300 | 2448 | 8176 | 102 | 154 |

All experiments were conducted in the presence of NRCO-4.

Example 7

Expression of antibiotic substances by CCTM. Skin biopsies, HF cultures, virus preparation, and virus transduction are as in example 1. The CCTM were collected from the tissue culture and medium and replated as a homogeneous population of cells in serum-free medium. The serum-free conditioned medium was harvested after four days of incubation in a $CO_2$ incubator at 37 degrees centigrade. Similarly treated serum-free media that did not include CCTM served as control. The results describing the action of antibiotic substances on bacteria-seeded chocolate agar plates are outlined in Table 6. The results describing the effects of titrating the serum-free conditioned media from CCTM with TSB on bacterial growth are outlined in Table 7. The results describing the effects of titrating the serum-free conditioned media from CCTM with serum-free control media on bacterial growth are outlined in Table 8.

TABLE 6

Effect of Serum-Free Conditioned Media From CCTM On Bacterial Growth In Agar Plates

| | |
|---|---|
| Haemophilus parainfluenzae ATCC 7901 | 0 mm |
| H. influenzae ATCC 19418 | 0 mm |
| Neisseria meningitidis ATCC 13090 | 0 mm |
| N. gonorrhoeae ATCC 33541 | 0 mm |
| N. gonorrhoeae PPNG ATCC 31426 | 0 mm |
| N. lactamica ATCC 23970 | 28 mm |
| Moraxella catarrhalis ATCC 25238 | 30 mm |
| Streptococcus pneumoniae ATCC 6303 | 28 mm |
| S. pyogenes ATCC 19615 | 32 mm |
| S. agalactiae ATCC 12386 | 0 mm |
| S. avium ATCC 14025 | 0 mm |
| Enterococcus faecalis ATCC 29212 | 0 mm |
| Staphylococcus aureus ATCC 25912 | 29 mm |
| Escherichia coli ATCC 25922 | 0 mm |
| Proteus vulgaris ATCC 13315 | 0 mm |
| Pseudomonas aeruginosa ATCC 27853 | 0 mm |

*No effect was seen with SFMC

TABLE 7

Effect of Serum-Free Conditioned Media From CCTM Titrated With TSB On Bacterial Growth

| | Prep. 1 | Prep. 2 |
|---|---|---|
| N. lactamica ATCC 23970 | 1:1 | 1:1 |
| Moraxella catarrhalis ATCC 25238 | 1:1 | 1:2 |
| Streptococcus pneumoniae ATCC 6303 | 1:1 | 1:16 |
| S. pyogenes ATCC 19615 | 1:1 | 1:2 |
| Staphylococcus aureus ATCC 25912 | 1:1 | 1:2 |

*No growth occurred in sterility tube.

TABLE 8

Effect of Serum-Free Conditioned Media From CCTM Titrated With Serum-Free Control Media On Bacterial Growth

| | Prep. 3 | Prep. 4 |
|---|---|---|
| Corynebacterium A ATCC 49676 | 1:1 | 1:2 |
| C. pseudodiphtheria ATCC 10700 | 1:1 | 1:1 |
| N. lactamica ATCC 23970 | 1:1 | 1:1 |
| Moraxella catarrhalis ATCC 25238 | 1:1 | 1:8 |
| Streptococcus pneumoniae ATCC 6303 | 1:1 | 1:512 |
| S. pyogenes ATCC 19615 | 1:256 | 1:64 |
| Staphylococcus aureus ATCC 25912 | 1:1 | 1:512 |

*No growth occurred in sterility wells.

Example 8

Uptake and replication of L. major. PBMC of HIV-1 and hepatitis B seronegative donors were recovered after leukapheresis and Ficoll-Hypaque density gradient centrifugation and separated into monocyte and PBL fractions by countercurrent centrifugal elutriation. Monocyte suspensions were 90–95% pure by criteria of cell morphology on Wright-stained cytosmears, by granular peroxidase, and by non-specific esterase. Monocytes were cultured as adherent monolayers in 0.2 ml DMEM with 10% heat-inactivated AB+ human serum, 50 µg/ml gentamicin, 2 mM glutamine, and 1000 U/ml highly purified human rMCSF. CCTM were obtained as in example 1. The human monocytes and CCTM were exposed to L. major amastigotes at an MOI of 1 at 37° C. in polypropylene tubes. Samples of cell suspensions were removed at various times. Percent macrophages with intracellular amastigotes was estimated microscopic examination of Wright-stained cytosmears. Results are shown in Table 9 and are expressed as mean percent Leishmania-infected monocytes/CCTM±SEM for 4 to 8 observations on 2 to 4 cultures (800–1600 cells observed).

As shown in Table 9, CCTM were considerably more effective in taking up L. major and they also show a greater rate of intracellular replication. It should also be emphasized that monocytes, unlike CCTM, must be activated by MCSF in order to affect uptake and replication of L. major. The ability to take up Leishmania is unique to tissue macrophages in vivo and fibroblasts are unable to do the same.

TABLE 9

Uptake and Replication of L. major By Normal Human Monocytes and By CCTM

| time (hrs) | % infected cells | amastigotes/infected cell [mean ± sem, 4 experiments] |
|---|---|---|
| Human Monocytes | | |
| 0 | 0 | 0 |
| 1 | 24 ± 3 | 1.1 ± 0.2 |
| 2 | 28 ± 2 | 1.2 ± 0.3 |
| 4 | 32 ± 1 | 1.1 ± 0.4 |
| 8 | 30 ± 3 | 1.3 ± 0.3 |
| 16 | 32 ± 4 | 1.5 ± 0.4 |
| 32 | 43 ± 2 | 2.2 ± 0.2 |
| 64 | 28 ± 3 | 6.2 ± 1.3 |
| 128 | 43 ± 5 | 8.4 ± 1.7 |
| ST:FeSV-induced CCTM | | |
| 0 | 0 | 0 |
| 1 | 18 ± 3 | 1.1 ± 0.1 |
| 2 | 23 ± 2 | 1.2 ± 0.3 |
| 4 | 31 ± 2 | 1.1 ± 0.2 |
| 8 | 32 ± 3 | 1.6 ± 0.3 |
| 16 | 34 ± 5 | 1.8 ± 0.4 |
| 32 | 49 ± 3 | 3.1 ± 0.6 |
| 64 | 56 ± 2 | 6.7 ± 1.5 |
| 128 | 73 ± 4 | 9.4 ± 0.9 |

Collectively, these results demonstrate the expression of antimicrobial activity in CCTM. The most sensitive bacterial strains to date were:
Streptococcus pneumoniae; gram positive (ATCC 6303)
Streptococcus pyogenes; gram positive (ATCC 19615)
Staphylococcus aureus; gram positive (ATCC 25912)
Moraxella catarrhalis; gram negative (ATCC 25238)
Neisseria lactamica; gram negative (ATCC 23970)

Without further elaboration, the foregoing will so fully illustrate my invention that those skilled in the art will recognize or be able to ascertain, using no more than routine experimentation, and may adapt same for use under various conditions of service.

We claim:

1. A method for the de novo conversion of human fibroblasts (HF) to cells that demonstrate characteristics of tissue macrophages (CCTM), comprising the steps of:

a. obtaining a biopsy from an organ or tissue of a human subject;

b. establishing and growing an HF monolayer culture from the organ or tissue biopsy;

c. transducing the HF monolayer culture with ST:FeSV (FeLV);

d. harvesting the transduced cells floating in the culture media;

e. re-plating the harvested cells and characterizing the harvested cells as CCTM by electron microscopy, expression of macrophage associated antigens, expression of macrophage associated cytokines, cytolytic activity, production of antibiotic substances, or ability to allow uptake and replication of Leishmania.

2. A cell that demonstrates characteristics of tissue macrophages (CCTM) made in accordance with the method in claim 1.

* * * * *